(12) United States Patent
Ortiz et al.

(10) Patent No.: US 6,964,684 B2
(45) Date of Patent: Nov. 15, 2005

(54) ANNULOPLASTY DEVICES AND RELATED HEART VALVE REPAIR METHODS

(75) Inventors: Mark Ortiz, Milford, OH (US); Randy Whedon, Cincinnati, OH (US); Paul A. Spence, Louisville, KY (US)

(73) Assignee: Medtentia, Lund (SE)

( * ) Notice: Subject to any disclaimer, the term of this patent is extended or adjusted under 35 U.S.C. 154(b) by 0 days.

(21) Appl. No.: 10/787,581

(22) Filed: Feb. 26, 2004

(65) Prior Publication Data

US 2004/0167620 A1 Aug. 26, 2004

Related U.S. Application Data

(62) Division of application No. 10/145,416, filed on May 14, 2002, now Pat. No. 6,730,121, which is a division of application No. 09/610,784, filed on Jul. 6, 2000, now Pat. No. 6,419,696.

(51) Int. Cl.$^7$ .............................................. A61F 2/24
(52) U.S. Cl. .................................. 623/2.37; 623/2.11
(58) Field of Search ............................ 623/2.11, 1.36, 623/2.37, 2.38, 1.11, 1.22, 900; 606/200

(56) References Cited

U.S. PATENT DOCUMENTS

| 3,656,185 | A | 4/1972 | Carpentier ........................... 3/1 |
| 3,997,923 | A | 12/1976 | Possis ............................. 3/1.5 |
| 4,042,979 | A | 8/1977 | Angell ............................. 3/1.5 |
| 4,055,861 | A | 11/1977 | Carpentier et al. .............. 3/1.5 |
| 4,489,446 | A | 12/1984 | Reed ............................... 3/1.5 |
| 4,535,483 | A | 8/1985 | Klawitter et al. ............... 623/2 |
| 4,602,911 | A | 7/1986 | Ahmadi et al. ................. 623/2 |
| 4,863,460 | A | 9/1989 | Magladry ........................ 623/2 |
| 4,917,698 | A | 4/1990 | Carpentier et al. ............. 623/2 |
| 5,061,277 | A | 10/1991 | Carpentier et al. ............. 623/2 |
| 5,104,407 | A | 4/1992 | Lam et al. ....................... 623/2 |
| 5,163,953 | A | 11/1992 | Vince .......................... 623/2.11 |
| 5,201,880 | A | 4/1993 | Wright et al. ................... 623/2 |
| 5,306,296 | A | 4/1994 | Wright et al. ................... 623/2 |
| 5,607,471 | A | 3/1997 | Seguin et al. ................... 623/2 |
| 5,669,919 | A | 9/1997 | Sanders et al. ............. 606/148 |
| 5,674,279 | A | 10/1997 | Wright et al. ................... 623/2 |
| 5,716,397 | A | 2/1998 | Myers .............................. 623/2 |
| 5,776,189 | A | 7/1998 | Khalid ............................. 623/2 |
| 5,824,066 | A | 10/1998 | Gross .............................. 623/2 |
| 5,876,436 | A | 3/1999 | Vanney et al. .................. 623/2 |
| 5,888,240 | A | 3/1999 | Carpentier et al. ............. 623/2 |
| 5,908,450 | A | 6/1999 | Gross et al. .................... 623/2 |

(Continued)

FOREIGN PATENT DOCUMENTS

DE 19605042 A1 1/1998

(Continued)

Primary Examiner—Bruce E. Snow
(74) Attorney, Agent, or Firm—Wood, Herron & Evans, L.L.P.

(57) ABSTRACT

Devices for repairing and replacing a heart valve in various embodiments, the devices include at least first and second support rings connected together in a coiled configuration to abut opposite sides of a valve annulus. A replacement valve may be secured to the coil-shaped device. Various alternative fastening systems include suture fastening systems, mechanical fastening systems, shape memory alloy fastening systems and other fastening systems relying only on the resilience between adjacent coils. A method generally includes inserting a first end of the coil-shaped member through a valve annulus, rotating a first ring of the coil-shaped member into position on one side of the valve annulus and positioning at least a second ring of the coil-shaped member on an opposite side of the valve annulus.

6 Claims, 16 Drawing Sheets

U.S. PATENT DOCUMENTS

| | | | |
|---|---|---|---|
| 6,059,827 A | 5/2000 | Fenton, Jr. | 623/2 |
| 6,136,015 A * | 10/2000 | Kurz et al. | 606/191 |
| 6,183,512 B1 | 2/2001 | Howanec et al. | 623/2.36 |
| 6,348,068 B1 | 2/2002 | Campbell et al. | 623/2.36 |
| 6,402,781 B1 | 6/2002 | Langberg et al. | 623/2.36 |
| 6,458,153 B1 | 10/2002 | Bailey et al. | 623/1.24 |
| 6,705,585 B1 * | 3/2004 | Roy | 251/11 |

FOREIGN PATENT DOCUMENTS

| | | |
|---|---|---|
| WO | WO 95/16407 | 6/1995 |
| WO | WO 99/O4730 | 2/1999 |

* cited by examiner

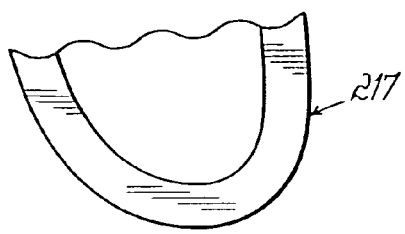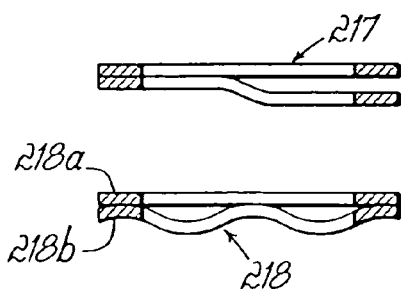
FIG. 29
FIG. 29A
FIG. 29B
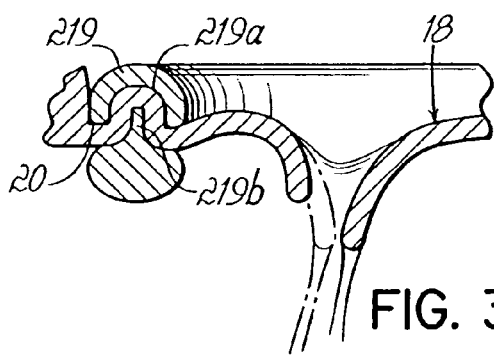
FIG. 30
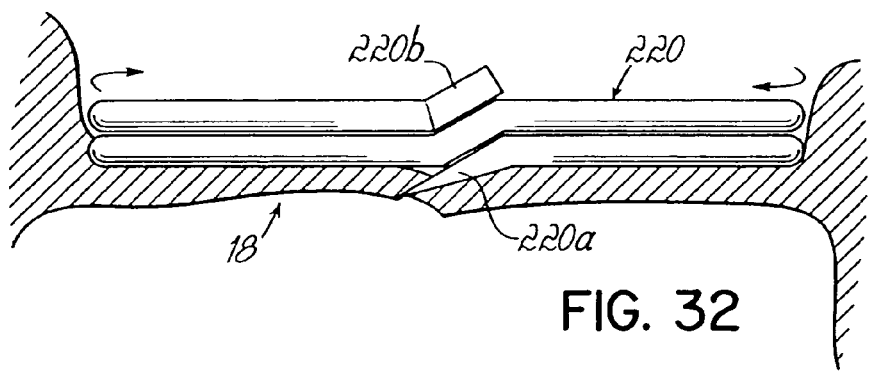
FIG. 32
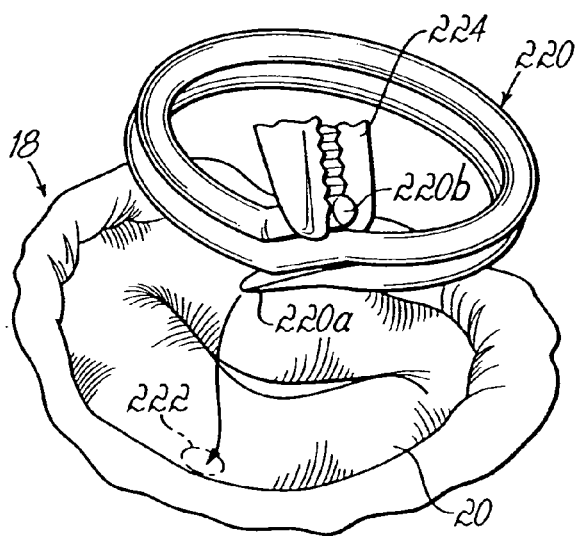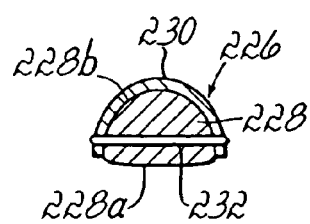
FIG. 31
FIG. 33

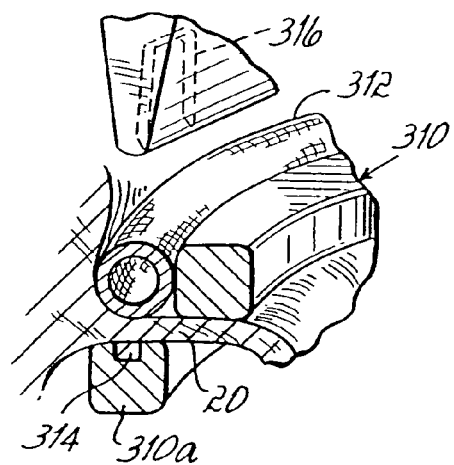
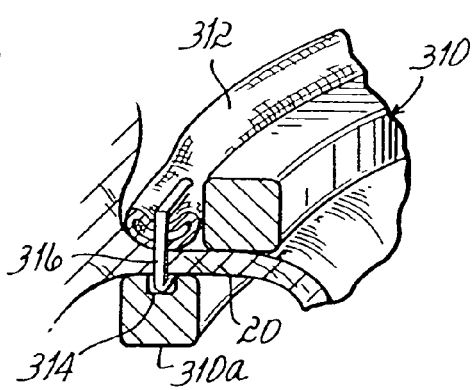
FIG. 41A  FIG. 41B
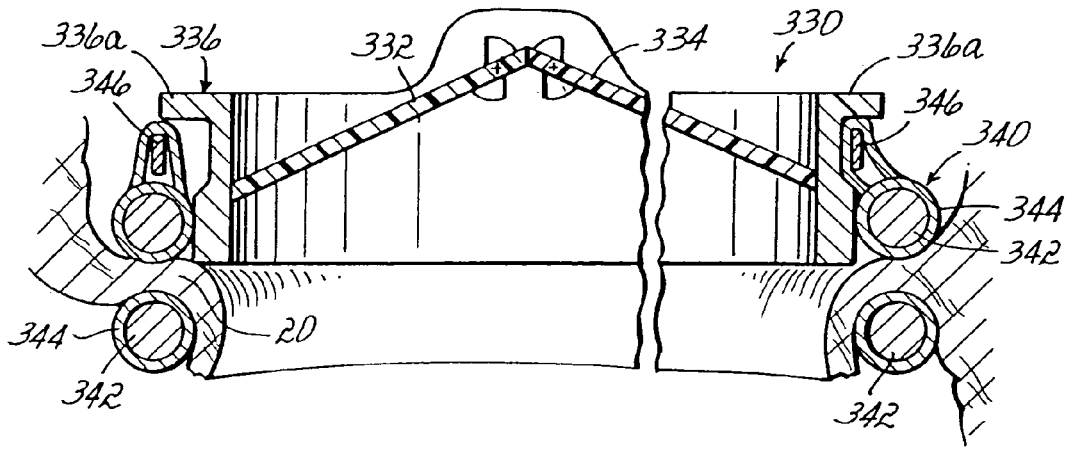
FIG. 42
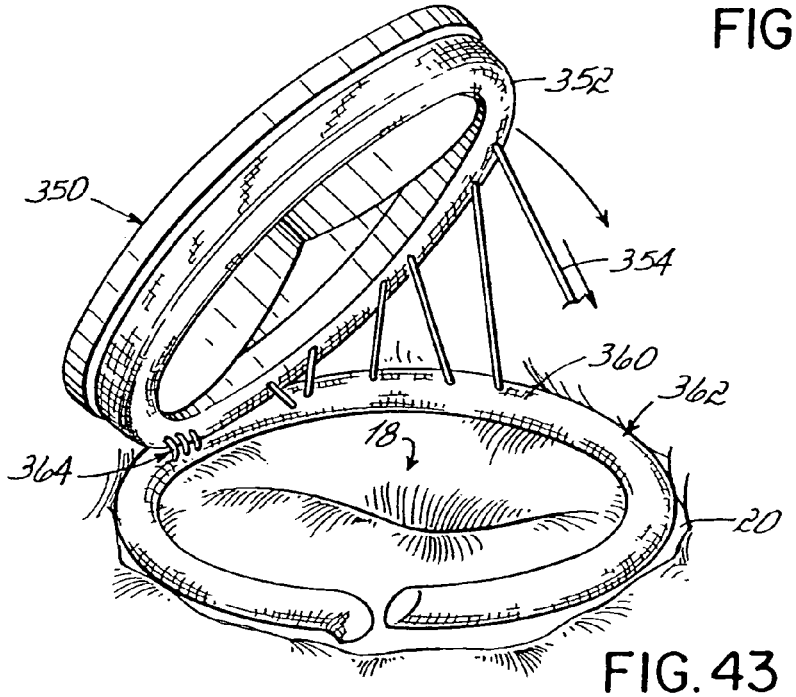
FIG. 43

ANNULOPLASTY DEVICES AND RELATED HEART VALVE REPAIR METHODS

This application is a divisional of application Ser. No. 10/145,416 filed on May 14, 2002 (now U.S. Pat. No. 6,730,121) which is a divisional of application Ser. No. 09/610,784 filed Jul. 6, 2000 (now U.S. Pat. No. 6,419,696), the disclosures of which are fully incorporated herein by reference.

FIELD OF THE INVENTION

The present invention generally relates to heart valve repair and replacement techniques and annuloplasty devices. More specifically, the invention relates to the repair and/or replacement of heart valves having various malformations and dysfunctions.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (insufficiency). The leaflets and chords may become calcified and thickened rendering them stenotic (obstructing forward flow). Finally, the valve relies on insertion of the chordae inside the ventricle. If the ventricle changes in shape, the valve support may become non-functional and the valve may leak.

Mitral and tricuspid valve replacement and repair are traditionally performed with a suture technique. During valve replacement, sutures are spaced around the annulus (the point where the valve leaflet attaches to the heart) and then the sutures are attached to a prosthetic valve. The valve is lowered into position and when the sutures are tied, the valve is fastened to the annulus. The surgeon may remove all or part of the valve leaflets before inserting the prosthetic valve. In valve repair, a diseased valve is left in situ and surgical procedures are performed to restore its function. Frequently an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, annuloplasty rings and replacement valves must be sutured to the valve annulus and this is time consuming and tedious. If the ring is severely malpositioned, then the stitches must be removed and the ring repositioned relative to the valve annulus during restitching. In other cases, a less than optimum annuloplasty may be tolerated by the surgeon rather than lengthening the time of surgery to restitch the ring.

During heart surgery, a premium is placed on reducing the amount of time used to replace and repair valves as the heart is frequently arrested and without perfusion. It would be very useful to have a method to efficiently attach a prosthesis into the mitral or tricuspid valve position. Furthermore such a method may have its greatest advantage in remotely attaching a valve repair or replacement device so that surgery could be avoided altogether.

Annuloplasty devices and methods and heart valve repair and replacement devices and techniques are therefore necessary to provide a more reliable and more easily accomplished valve repair and replacement.

SUMMARY OF THE INVENTION

The present invention generally provides a device for repairing a heart valve having an annulus and a plurality of leaflets for allowing and preventing blood flow through a patient's heart. The device comprises a first support ring and a second support ring connected to the first support ring to form a coiled configuration. The first support ring is configured to abut one side of the valve annulus and the second support ring is configured to abut an opposite side of the valve annulus to thereby trap valve tissue, that is, annulus tissue and/or leaflet tissue, therebetween. This device may be used in those situations, for example, that have conventionally utilized annuloplasty rings, but the device of this invention may be applied in a much easier manner. The device may also be used to carry a replacement heart valve. The invention contemplates various embodiments of the device, including embodiments for catheter-based surgery and embodiments for open heart surgery.

In the various embodiments, the first and second support rings may have an inner core covered by an outer layer, such as a fabric layer, with the inner core being formed from a more rigid material than the outer layer. The first and second support rings may have generally triangular-shaped cross sections with flat sides opposing one another and trapping valve tissue therebetween. A plurality of fasteners may be used between the first and second support rings and, for example, these may comprise sharp projections. An actuating member may be used to actuate the fasteners to an extended position through the valve tissue. Other forms of fasteners are possible as well, including those comprising projections and complimentary receiving members on the first and second support rings. Shape memory alloys may be used to facilitate connection, such as by moving the first and second support rings together or moving fastening elements thereof into engagement.

At least the opposed surfaces of the first and second support rings may be roughened, such as by the use of fabric, coatings, knurling or the like to facilitate better engagement and retention of the support rings on the valve tissue. A removable sleeve may be carried by the first and second support rings for initially reducing friction between the respective rings and the valve tissue during initial engagement therewith, such as during rotation of the device on either side of the annulus. The sleeve may then be removed to expose the higher friction surfaces of the device to the valve tissue for better retention.

Preferably, the first and second support rings are formed integrally from a coiled rod, such as a metallic rod, with one end of the rod formed as a leading end and one end formed as a trailing end. These ends may be bent in opposite directions so that the leading end may be directed through the valve tissue and the trailing end may be grasped by an appropriate surgical implement. A carrier may be used to rotate the device into position on opposite sides of the valve annulus and then may be removed leaving the first and second support rings in place to trap the valve tissue therebetween. As another alternative, the carrier may be coil-shaped and the repair device may be rotated into place on only one side of the valve annulus similar to conventional rings. The carrier may then be rotated for removal while leaving the repair device in place. The first and second support rings may be adjustable in diameter to allow adjustment of the valve annulus.

When replacing a heart valve, a device of this invention again preferably comprises first and second support rings formed in a coiled configuration with a replacement valve coupled to at least one of the support rings. The replacement valve may be coupled in a releasable manner using any suitable fastening structure. For example, the replacement valve and one of the support rings may include mating engagement elements or the replacement valve may be directly threaded into one of the support rings. The replacement valve and one of the support rings may alternatively include respective cuffs adapted to receive sutures to fasten the replacement valve to the support ring. Optionally, one of the support rings may include a cuff with a movable fastening element which is engageable with the replacement valve. The fastening element may be formed from a shape memory alloy to facilitate its movement between an engaged and a disengaged position relative to the replacement valve.

The invention further contemplates various methods of repairing a heart valve including methods for fully replacing the heart valve. Generally, the method includes inserting a first end of a coil-shaped support through the tissue of a heart valve. A first ring of the coil-shaped support is then rotated in position on a first side of the annulus and a second ring of the coil-shaped support is positioned on an opposite side of the annulus. The first and second rings may then be fastened together to trap the annulus tissue therebetween, or the inherent resilience between the first and second rings may trap tissue without using separate fasteners. The coil-shaped support may be carried in its coiled form during the rotation step, or the coil-shaped support may be extended from a catheter positioned adjacent the annulus. Many other variations of these methods and additional methods will be apparent to those of ordinary skill upon review of this disclosure.

Various additional objectives, advantages and features of the invention will become more readily apparent to those of ordinary skill in the art upon review of the detailed description of the illustrative embodiments.

BRIEF DESCRIPTION OF THE DRAWINGS

FIG. 29 is a plan view of another alternative heart valve repair device.

FIG. 29A is a transverse cross sectional view of the repair device shown in FIG. 29.

FIG. 29B is a transverse cross sectional view similar to FIG. 29A, but illustrating another alternative configuration.

FIG. 30 is a cross sectional view of another alternative fastening structure for devices of the present invention.

FIG. 31 is a perspective view, illustrating another alternative heart valve repair device being applied to a mitral valve.

FIG. 32 is a side view of the device shown in FIG. 31 shown being applied around the mitral valve annulus.

FIG. 33 is a transverse cross sectional view of an alternative construction of the coil-shaped repair device of this invention.

FIGS. 41A and 41B are cross sectioned perspective views illustrating the steps in applying another alternative repair device to a heart valve.

FIG. 42 is a cross sectional view showing another alternative heart valve repair device applied to a heart valve annulus.

FIG. 43 is a perspective view showing another alternative heart valve replacement device in accordance with the invention.

DETAILED DESCRIPTION OF THE PREFERRED EMBODIMENTS

Figure 1:
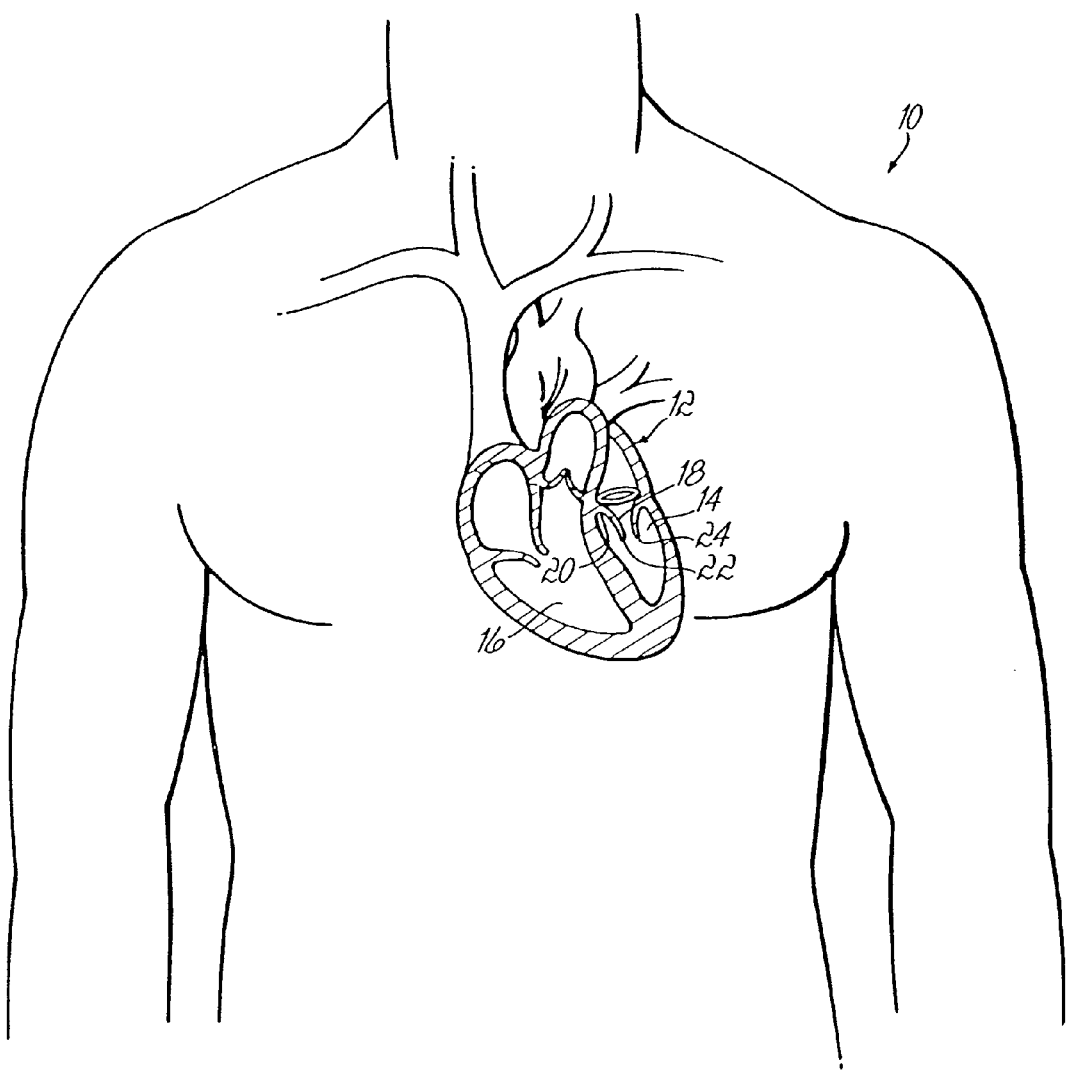
FIG. 1 schematically illustrates a patient with a heart shown in cross section and a device of the present invention schematically illustrated as supporting the mitral valve.
Figure 1A:
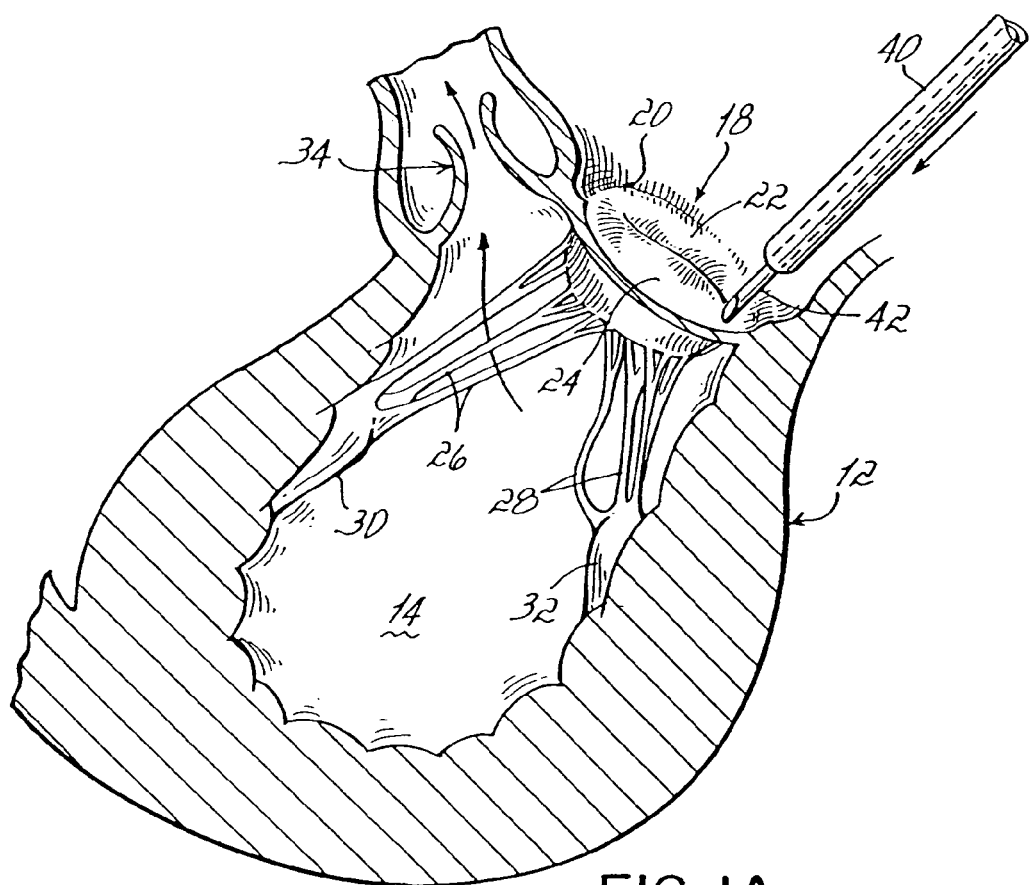
FIG. 1A is a cross sectional view of the left ventricle showing the mitral valve and a catheter-based device of the invention in perspective.

FIG. 1 illustrates a patient 10 having a heart 12 shown in cross section including a left ventricle 14 and a right ventricle 16. The concepts of the present invention are suitable to be applied, for example, to a mitral valve 18 which supplies blood into left ventricle 14. Mitral valve 18, as better shown in FIG. 1A, includes an annulus 20 and a pair of leaflets 22, 24 which selectively allow and prevent blood flow into left ventricle 14. It will be appreciated that the term annulus tissue is used extensively throughout this disclosure in reference to the drawings, however, the inventive principles are equally applicable when referring to other valve tissue such as leaflet tissue or other attached vessel tissue. Leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present invention is applicable to heart valves other than the mitral valve in various of its aspects to be described below.

Figure 2A:
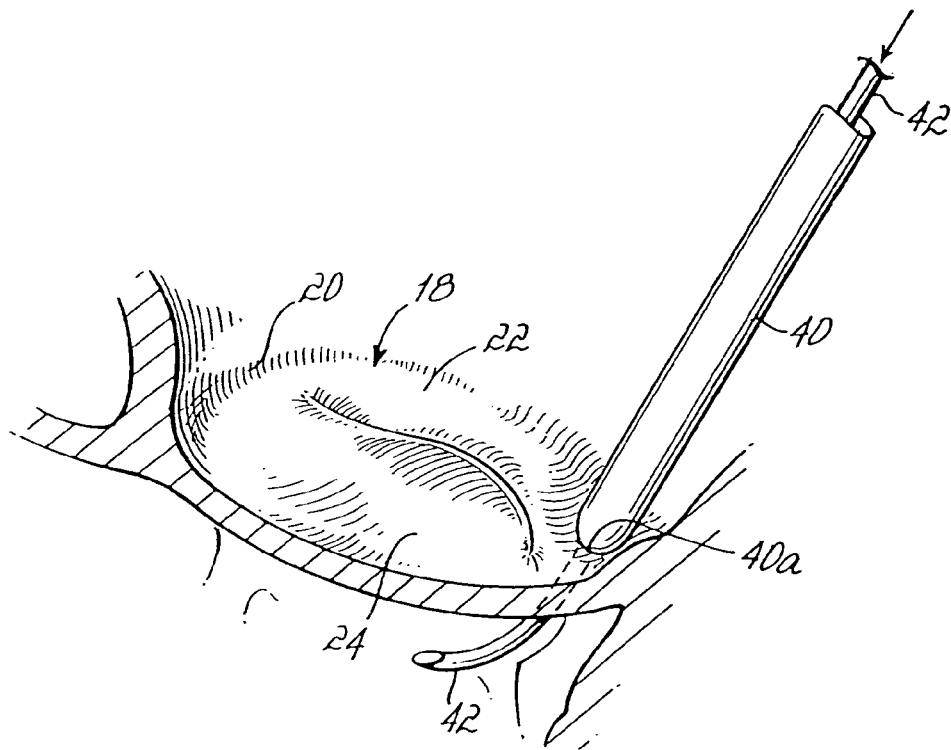
FIG. 2A is a partially sectioned perspective view of the mitral valve and the catheter-based device during the insertion procedure.
Figure 2B:
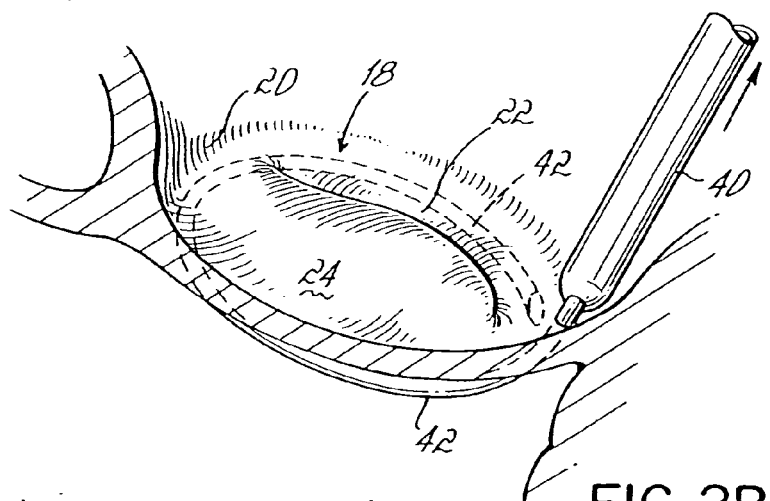
FIG. 2B is a view similar to FIG. 2A showing the device fully inserted beneath the mitral valve.
Figure 2C:
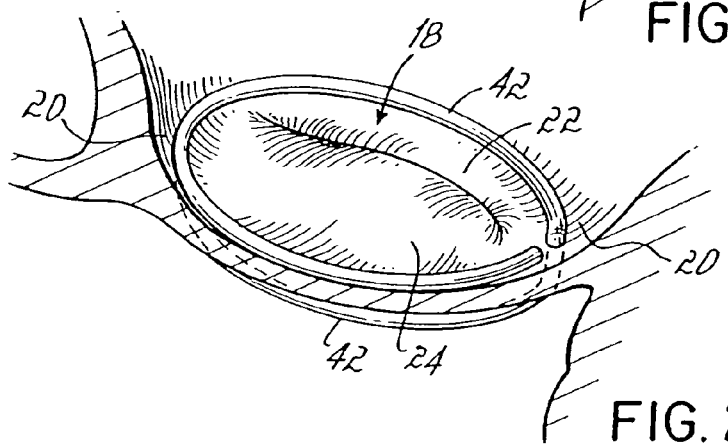
FIG. 2C is a view similar to FIG. 2B, but illustrating the device fully attached to the mitral valve.
Figure 3:
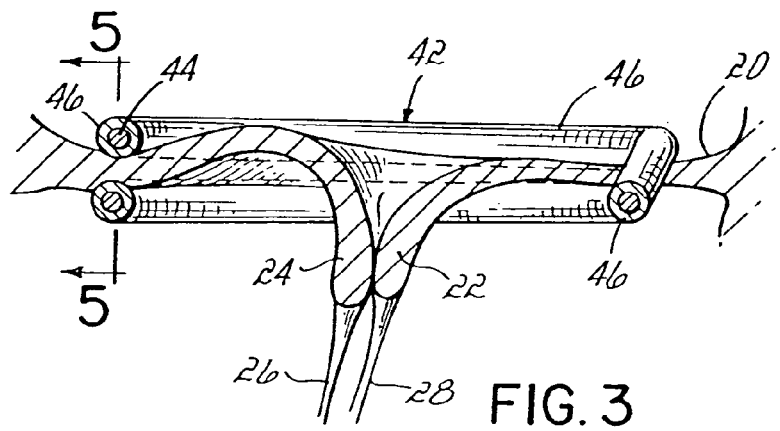
FIG. 3 is a transverse cross sectional view of the device shown in FIG. 2C.
Figure 4:
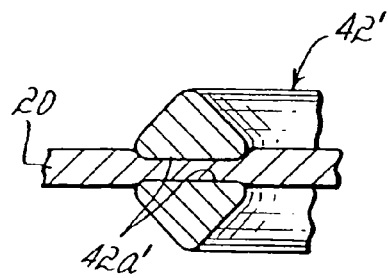
FIG. 4 is a cross sectional view of another embodiment of the repair device.

One preferred device of the present invention is shown in FIGS. 2A–2C and FIG. 3 and is applied through the use of a catheter 40 inserted into the appropriate region of heart 12, such as above mitral valve 18, by conventional techniques such as through a femoral artery. A flexible elongate support member 42 is contained in a movable manner within catheter 40 and, when extended therefrom as shown in FIGS. 2A–2C, assumes a spiral or keyring-type configuration. Any suitable medical grade material(s), such as medical grade metals or plastics, may be used to form elongate support member 42. One form is shown in cross section in FIG. 3 and comprises an inner core 44 surrounded by an outer layer 46. Inner core 44 may be formed from a more rigid material, such as metal or plastic, while outer layer 46 may be formed from a softer layer, such as fabric. Another alternative flexible elongate support member 42' is shown in FIG. 4. This embodiment has a traditional cross sectional shape associated with a keyring. In this embodiment flat, opposed surfaces 42a' trap valve annulus tissue 20 therebetween.

As shown in FIG. 2A, catheter 40 is inserted until an open end 40a thereof is positioned adjacent annulus 20. Support member 42 is then extended through annulus 20 and pushed outward from catheter 40 to assume its pre-stressed coiled shape beneath mitral valve 18 generally adjacent annulus 20 as shown in FIG. 2B. As further shown in FIG. 2B, catheter 40 is then withdrawn with respect to support member 42 to release the remaining portion of support member 42 into the pre-stressed coiled shape above mitral valve 18 such that annulus 20 is trapped between adjacent coils of support member 42.

Figure 5A:
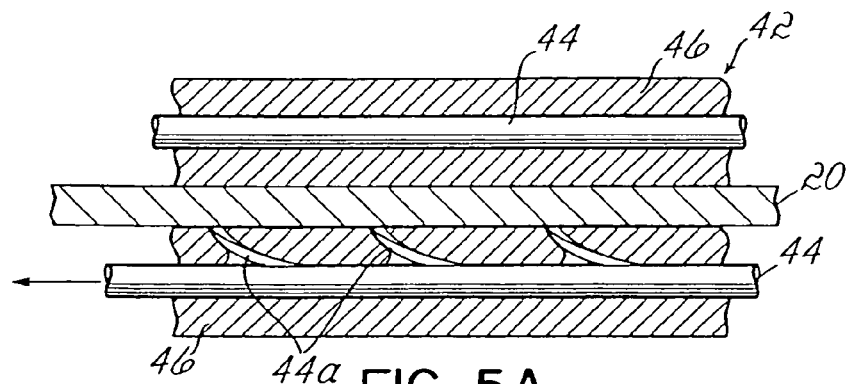
FIG. 5A is a cross sectional view, partially fragmented, to show one version of a fastening system for devices of the present invention.
Figure 5B:
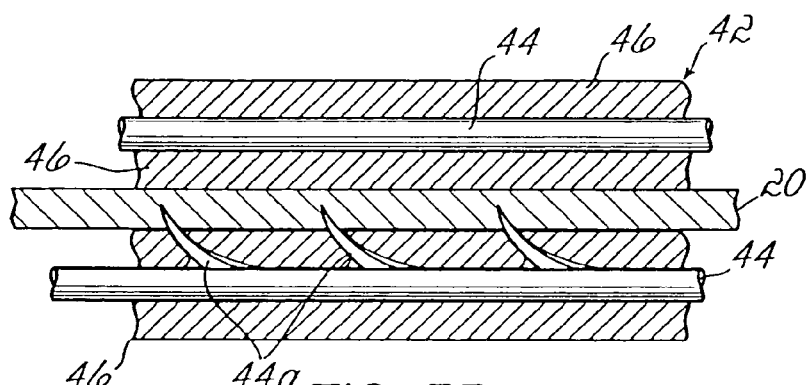
FIG. 5B is a cross sectional view similar to FIG. 5, but illustrating engagement of the fasteners with the valve tissue.
Figure 6:
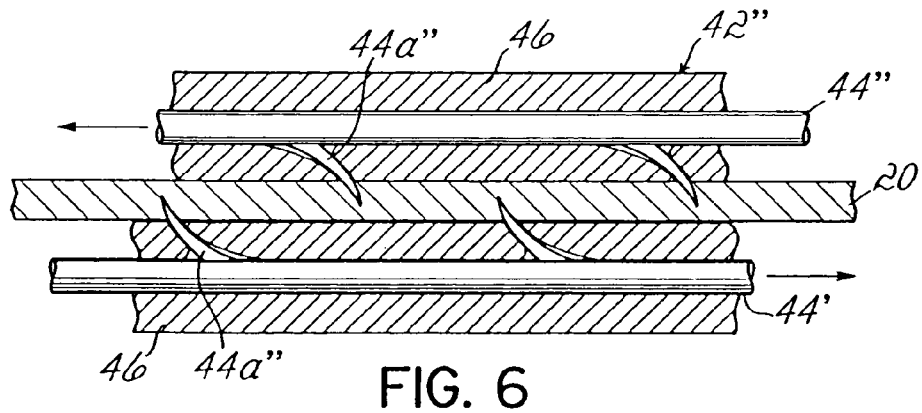
FIG. 6 is a cross sectional view similar to FIG. 5B, but illustrating another alternative fastening system.

FIGS. 5A and 5B illustrate an embodiment of support member 42 in which internal core 44 includes barbs 44a which are movable between extended and retracted positions. In the retracted position shown in FIG. 5A, barbs 44a do not engage valve annulus tissue 20. When internal core 44 is pulled in the direction of the arrow in FIG. 5A, barbs 44a extend through outer layer 46 and into valve annulus 20. This retains flexible elongate support member 42 in place on valve annulus 20. FIG. 6 illustrates another embodiment of a flexible elongate support member 42".

In this embodiment, internal core 44" includes barbs 44a" extendable from opposite directions into valve annulus 20 upon pulling the internal core 44" in the direction shown by the arrows to facilitate additional securement.

Figure 6A:
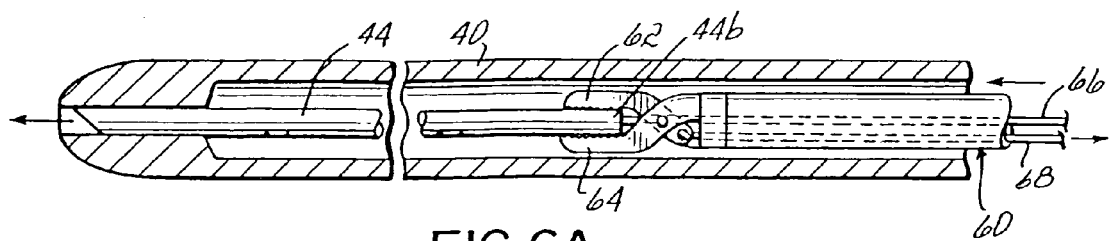
FIG. 6A is a partially fragmented, cross sectional view of the catheter repair device.
Figure 6B:
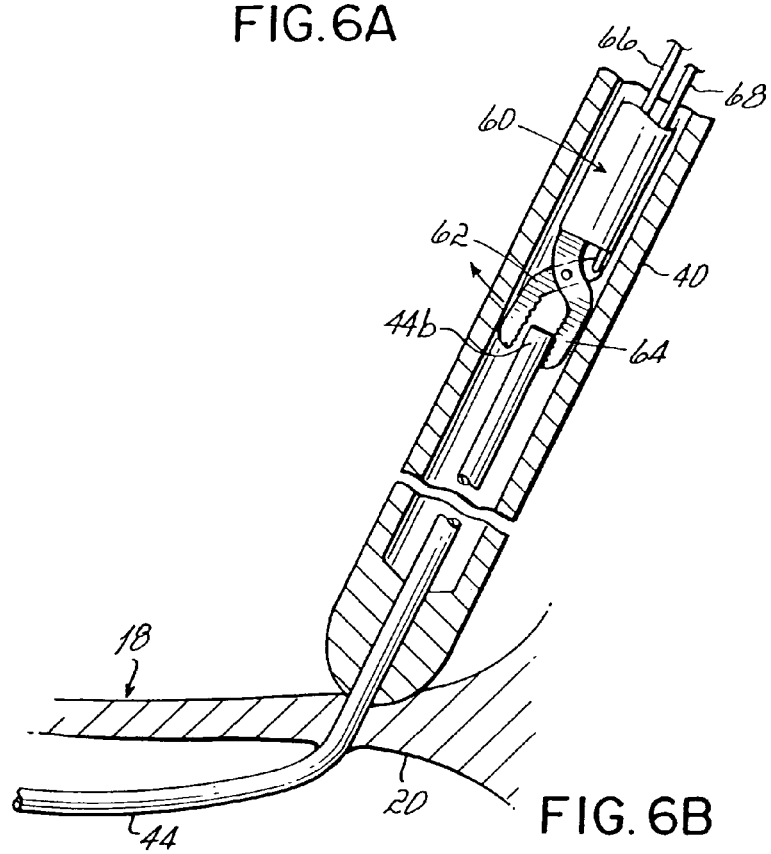
FIG. 6B is a partially fragmented, enlarged cross sectional view illustrating the device of FIG. 6A inserting the heart valve repair device.

FIGS. 6A and 6B illustrate cross sections of the catheter 40 and inner core 44 and one schematically illustrated actuation device 60. Specifically, a pair of jaws 62, 64 may be pivotally secured together and actuated between open and closed positions using cables 66, 68 to grip one end 44b of the inner core 44. The actuation device 60 may then be pulled or pushed by the surgeon in the appropriate direction to extend or retract the barbs 44 (FIG. 5A).

Figure 7:
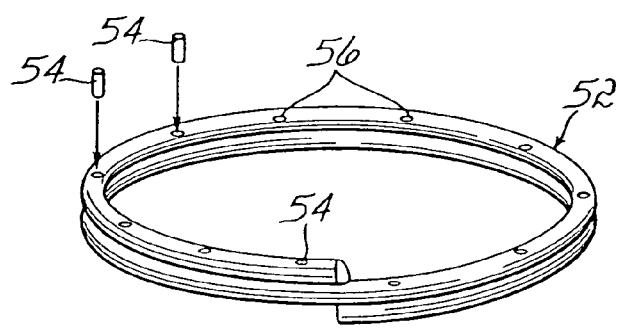
FIG. 7 is a perspective view of another alternative heart valve repair device.

FIG. 7 illustrates another embodiment of a flexible elongate support member 52 in the shape of a coil or, in other words, generally the shape of a keyring. In this embodiment, separate retaining members 54 may be inserted through respective holes 56 in adjacent coils of support member 52 to retain annulus tissue (not shown) therebetween. Retaining members 54 may be threaded or unthreaded pins and may be integrated directly into support member 52 for actuation between locking and unlocking positions relative to the valve annulus.

Figure 8:
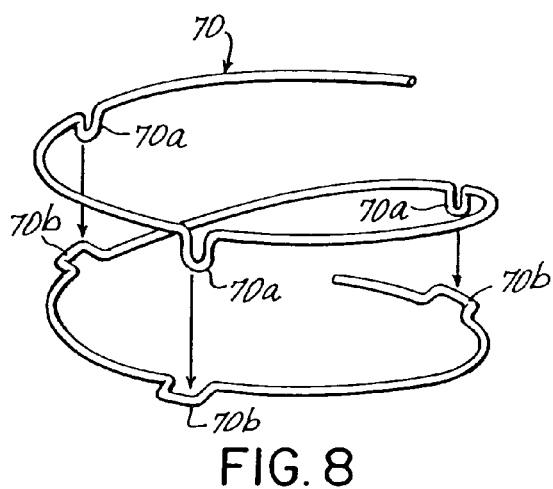
FIG. 8 is a perspective view of another alternative valve repair device in a deactivated state.
Figure 9:
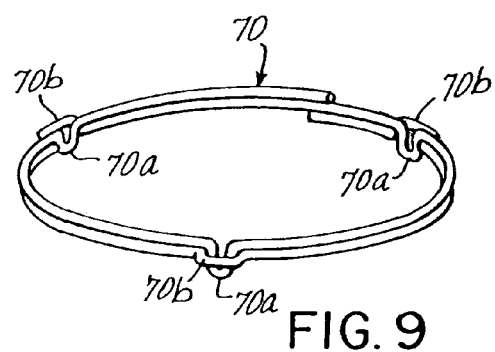
FIG. 9 is a perspective view of the device shown in FIG. 8, but illustrating the activated state.

FIGS. 8 and 9 illustrate another embodiment of a coiled support member 70 in which the support member includes interlocking portions 70a, 70b. As one example, the coiled support member 70 may be inserted in a manner similar to the method described in connection with FIGS. 2A–2C and once inserted on opposite sides of the valve annulus, the coiled support member 70 may be activated to a locked position as shown in FIG. 9. For example, the coiled support member 70 may be formed from a shape memory alloy and may be activated between the unlocked position shown in FIG. 8 and the locked position shown in FIG. 9 through the application of suitable electric current.

Figure 10:
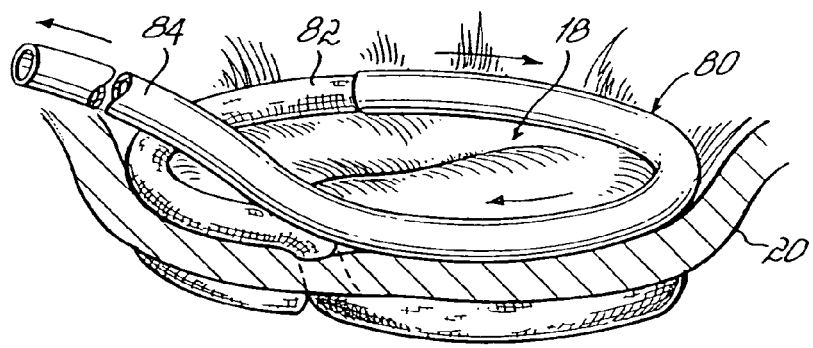
FIG. 10 is a partially cross sectioned perspective view illustrating another embodiment of the heart valve repair device.
Figure 11:
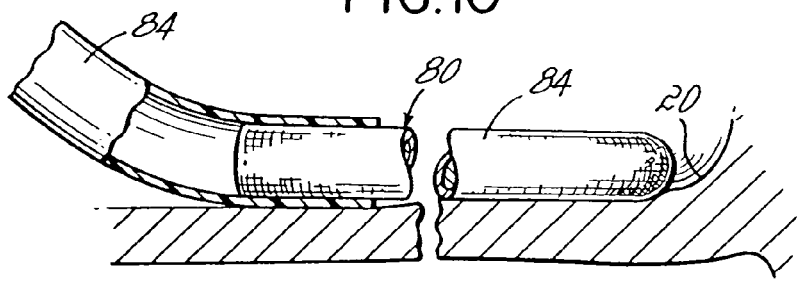
FIG. 11 is an enlarged partial cross sectional view illustrating the device of FIG. 10.

FIGS. 10 and 11 illustrate another alternative coil-shaped valve support member 80 which may again comprise an inner core (not shown) surrounded by an outer layer 82 of flexible fabric. In such constructions, the friction created by the outer layer 82 may make insertion of the coil member 80 difficult, especially in cases in which coil member 80 is simply manually turned into position as described below. Therefore, in this embodiment a sleeve 84 is provided on the outside of the coil member 80. The sleeve 84 is formed of a low friction material such as PTFE or Teflon®, or another similar material. This low friction material will make insertion of the coil member 80 easier by simply rotating the coil member 80 into place through a suitable slit or hole formed through the valve annulus 20. Once the coil member 80 is inserted as shown in FIG. 10, the sleeve 84 may be pulled off of the coil member 80 and discarded. Alternatively, sleeve 84 may be a coating that is absorbable or that may be rinsed off after fulfilling its function of easing insertion.

Figure 12:
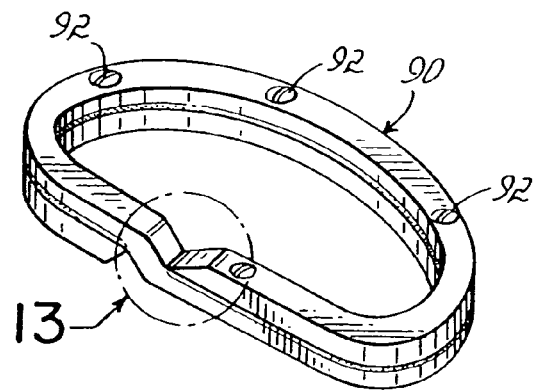
FIG. 12 is a perspective view of another alternative heart valve repair device.
Figure 13:
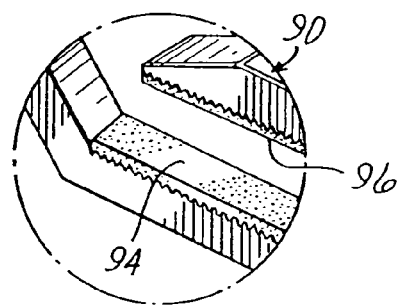
FIG. 13 is an enlarged view of encircled portion 12A of FIG. 12 showing the coils separated.

FIGS. 12 and 13 illustrate another alterative valve support member 90 in the shape of a coil or keyring. This embodiment also illustrates retaining members 92 in the form of small threaded fasteners as generally described in connection with FIG. 7. As shown best in FIG. 13, a coating of softer cushioning material 94, 96 may be applied to surfaces of the coil member 90 which oppose one another and contact opposite sides of the valve annulus (not shown). In addition to cushioning the contact areas with the annulus tissue, these coatings 94, 96 may provide additional friction to retain the coil member 90 in place. Again, a low friction sleeve (not shown) may be used as described in connection with FIGS. 10 and 11 to ease insertion of coil member 90 above and below the valve.

Figure 14:
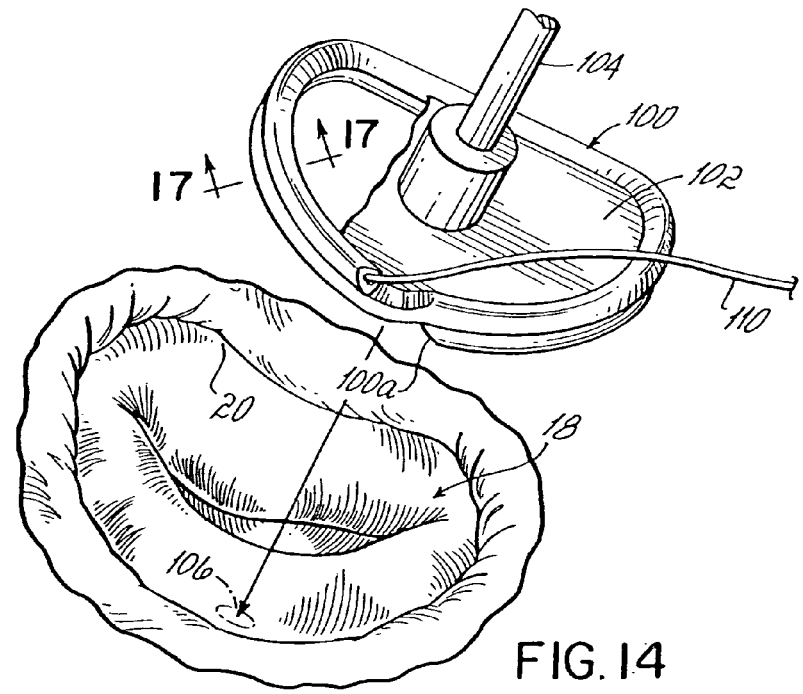
FIG. 14 is a perspective view illustrating the application of a heart valve repair device of the present invention to a mitral valve.
Figure 15:
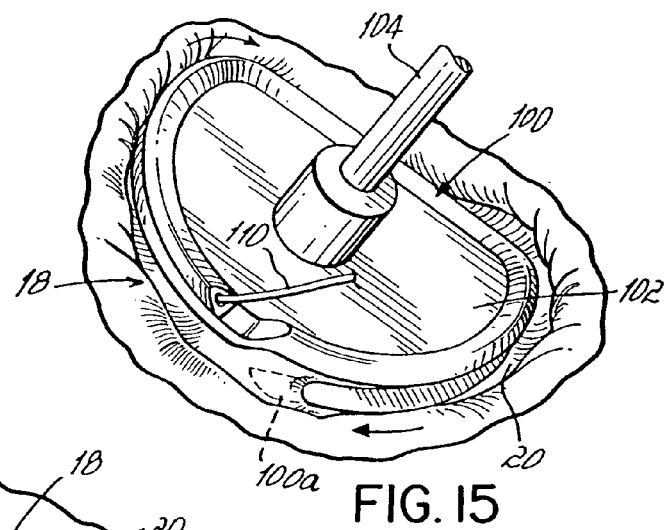
FIG. 15 is a perspective view similar to FIG. 14, but illustrating insertion of the leading end of the device into the valve annulus.
Figure 16:
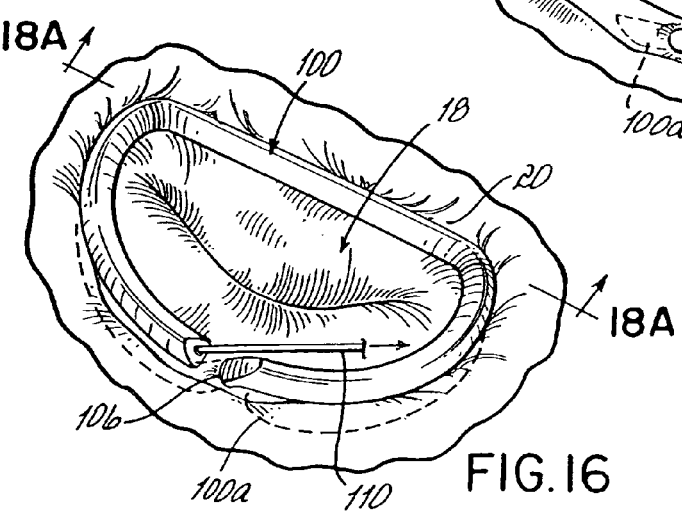
FIG. 16 is a perspective view similar to FIG. 15, but illustrating the repair device fully applied to the valve.

FIGS. 14–16 illustrate another alternative for installing a coil member 100 constructed generally in accordance with the invention. A temporary holder 102 is coupled between the coils and includes a handle portion 104 for allowing rotation of coil member 100 about a central axis defined generally along the length of handle portion 104. A small incision or hole 106 is made in annulus 20 as shown in FIG. 14 and a starting end 100a of the coil member 100 is inserted through the incision 106 as shown in FIG. 15. Handle portion 104 is rotated until at least approximately one coil is beneath the valve 18 and one coil remains above the valve 18 to trap the annulus tissue 20 therebetween as generally described above and as shown in FIG. 16.

Figure 17:
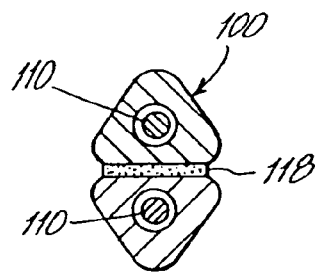
FIG. 17 is a cross sectional view taken along line 17—17 of FIG. 14.
Figure 18A:
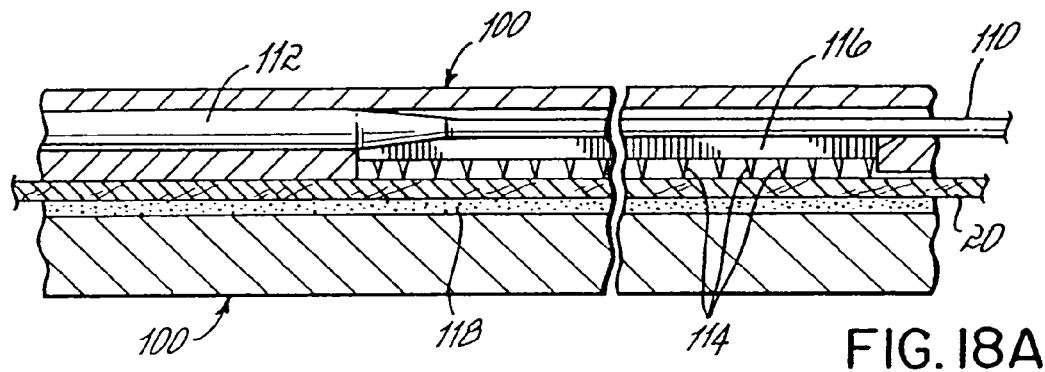
FIG. 18A is a cross sectional view taken along line 18—18 of FIG. 16, illustrating one fastening system of the invention is a deactivated state.
Figure 18B:
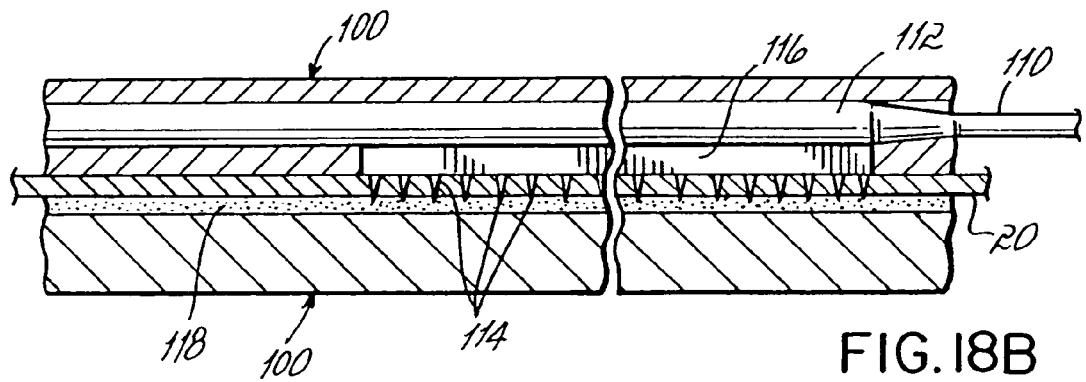
FIG. 18B is a cross sectional view similar to FIG. 18A, but illustrating the activated state of the fastening system.

FIGS. 17 and 18A–18B illustrate another alternative locking structure usable with the embodiment shown in FIGS. 14–16. In this regard, a core 110 may be pulled and used to actuate a cam mechanism 112 to drive a series of barbs or other fastening members 114 connected to a carrier 116 through the annulus tissue 20 and, optionally, into a soft coating 118, such as silicone, disposed on the opposite coil. The core 110 may then be cut and knotted to prevent movement thereof in the opposite direction such that the cam mechanism 112 retains the barbs or other fastening members 114 in the position shown in FIG. 18B.

Figure 19:
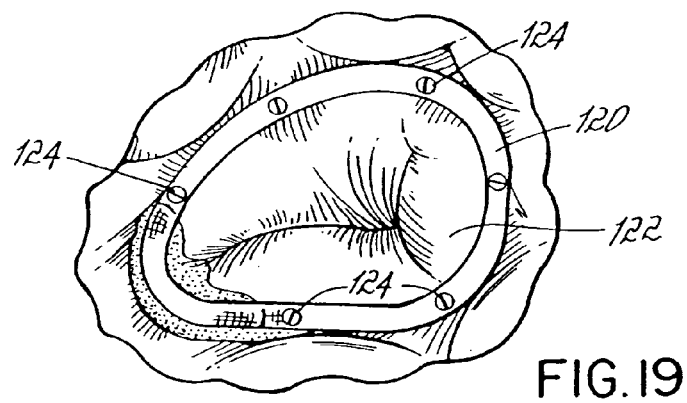
FIG. 19 is an elevational view of a heart valve repair device of the present invention applied to a tricuspid valve.

FIG. 19 illustrates a valve support member 120 specifically configured for a tricuspid valve 122 and which may be otherwise formed as a coil as generally discussed herein, and by including fasteners or locking elements 124.

Figure 20:
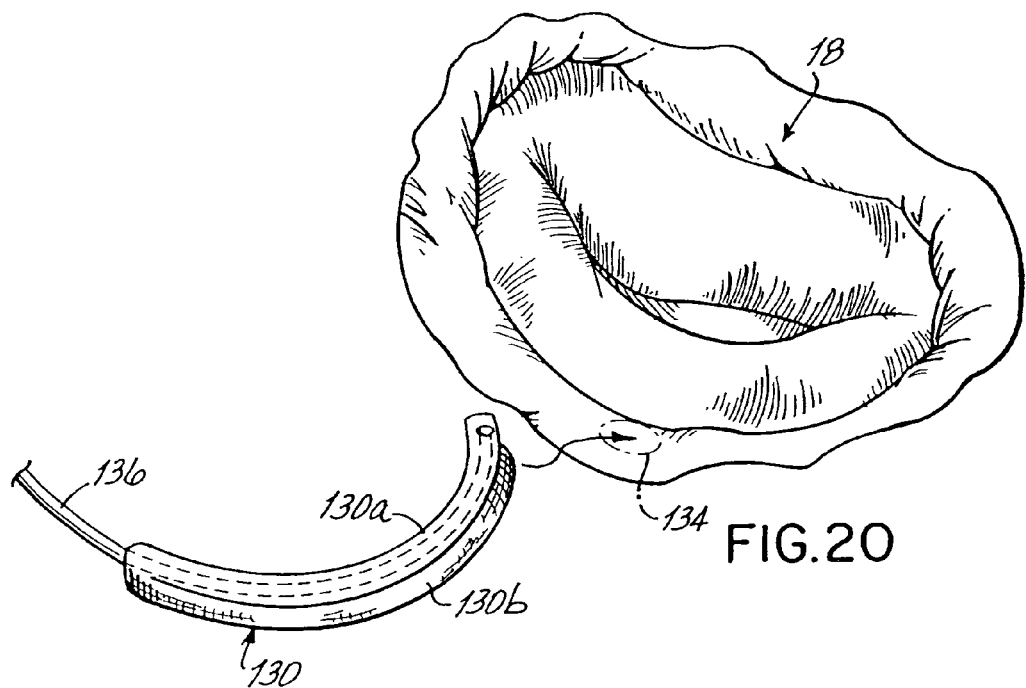
FIG. 20 is a perspective view illustrating another repair device of the present invention being applied to a mitral valve.
Figure 21:
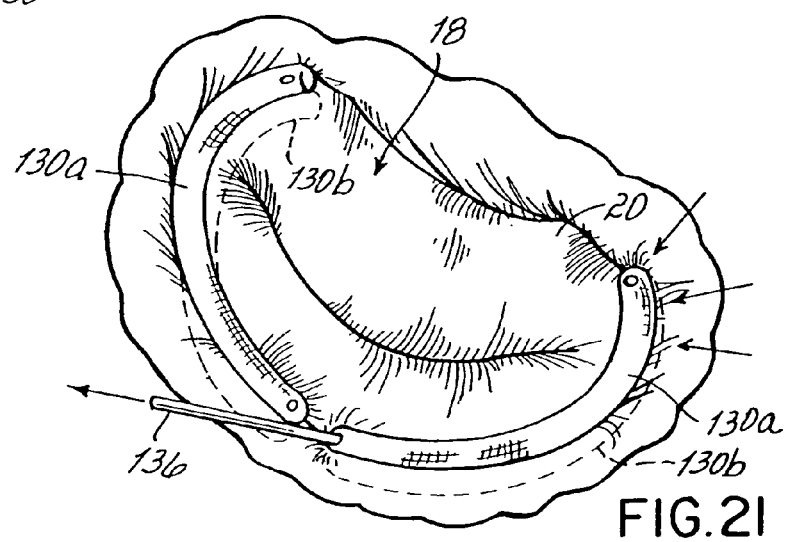
FIG. 21 is a view similar to FIG. 20, but illustrating two of the devices applied to the mitral valve.

FIGS. 20 and 21 illustrate generally C-shaped support members 130 which include first and second connected legs 130a, 130b for locking on opposite sides of a valve, such as a mitral valve 18, as shown in FIG. 21. Each C-shaped valve support member 130 is inserted through an incision 134 such that legs 130a, 130b trap annulus tissue 20 therebetween as shown in FIG. 20. A core 136 is used to activate a locking mechanism (not shown), such as the mechanisms previously described.

Figure 22:
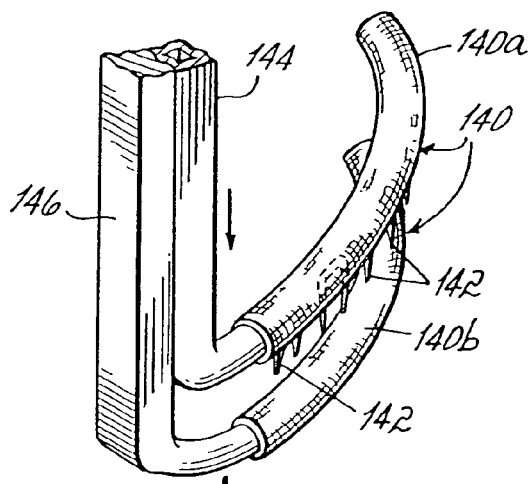
FIG. 22 is a partially fragmented perspective view of another alternative heart valve repair device of the invention.

FIG. 22 illustrates another alternative locking mechanism used on a generally C-shaped valve support member 140. In this embodiment, the two opposing legs 140a, 140b are moved relatively toward each other such that a plurality of locking elements or barbs 142 engage the valve tissue (not shown) therebetween. Handle or actuating portions 144, 146 may then be removed by the surgeon.

Figure 23:
FIG. 23 is a perspective view of another alternative heart valve repair device.

FIG. 23 illustrates a removable fabric sleeve 150 usable with or without the internal, more rigid portion 152 of a coil valve support member.

Figure 24:
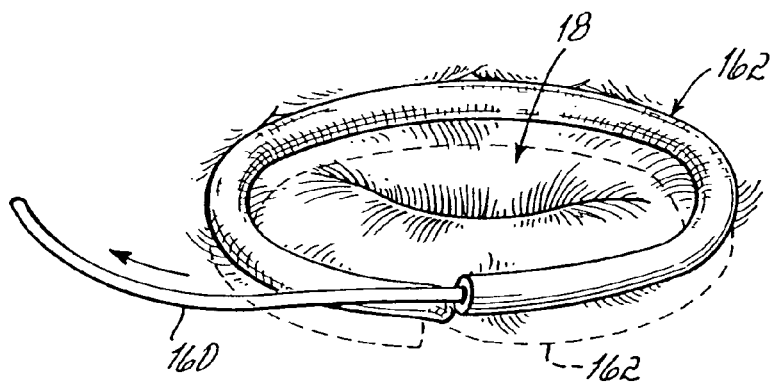
FIG. 24 is a perspective view of another alternative heart valve repair device.
Figure 25:
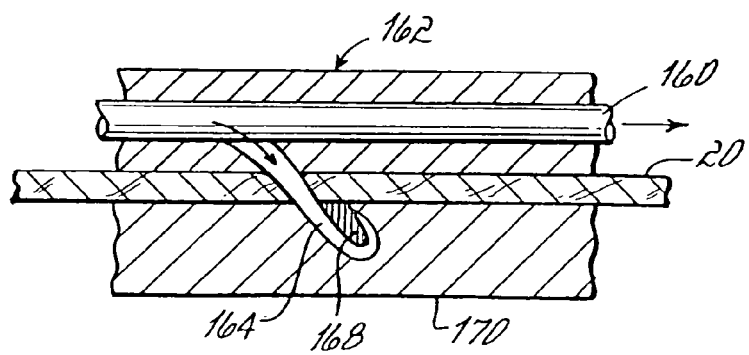
FIG. 25 is a fragmented, cross sectional view showing another alternative fastening system for repair devices of the invention.

FIGS. 24 and 25 illustrate another alternative locking mechanism usable with coil valve support members of the present invention. In this regard, a core 160 of coil member 162 actuates a flexible barb member 164 through the annulus tissue 20 and into an anvil portion 168 in an opposed coil portion 170. This effectively locks the barb member 164 into a hook shape within anvil portion 168 as shown to provide a more effective locking action.

Figure 26:
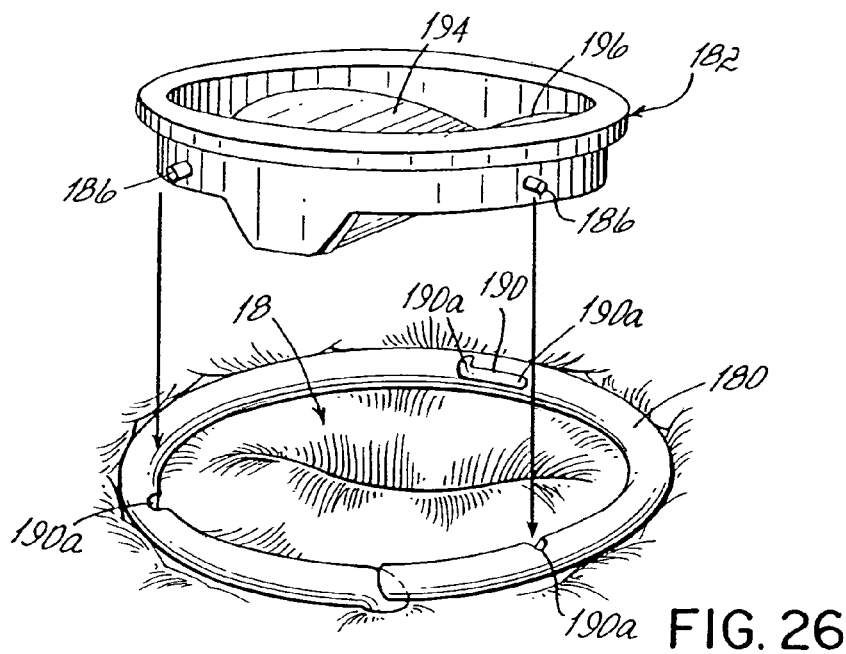
FIG. 26 is an exploded perspective view of one heart valve replacement device of the present invention.
Figure 27:
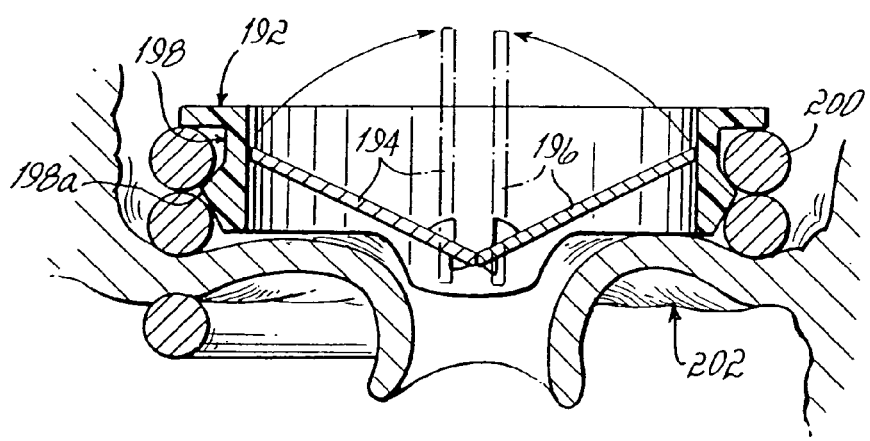
FIG. 27 is a transverse cross sectional view of another alternative heart valve replacement device.

FIG. 26 illustrates another alternative embodiment of the invention utilizing a coil-type support member 180 for anchoring a replacement heart valve 182 in place once the coil-type support member 180 is turned into place around the native valve annulus and fixed into place, such as previously described, the native mitral valve 18 or other valve is cut away and replacement valve 182 may be locked onto the coil-type support member 180. The replacement valve 182 may be conventional or of any desired design and, in accordance with the invention, may include various types of connecting members for making the connection between the valve 182 and the support member 180. In the embodiment shown in FIG. 26, this connection is made by projections 186 on the valve 182 which register with grooves, recesses or other slots 190 of support member 180. The projections 186 are inserted into one portion 190a of each slot 190 and turned to the end 190b of the slot as shown. FIG. 27 illustrates a similar replacement valve 192, such as a valve having movable flaps 194, 196. The outer, annular portion 198 of the valve 192 includes an outer surface 198a which maybe be essentially threaded into a coil support member 200 such that it is secured in place above the native valve 202 as shown.

Figure 28:
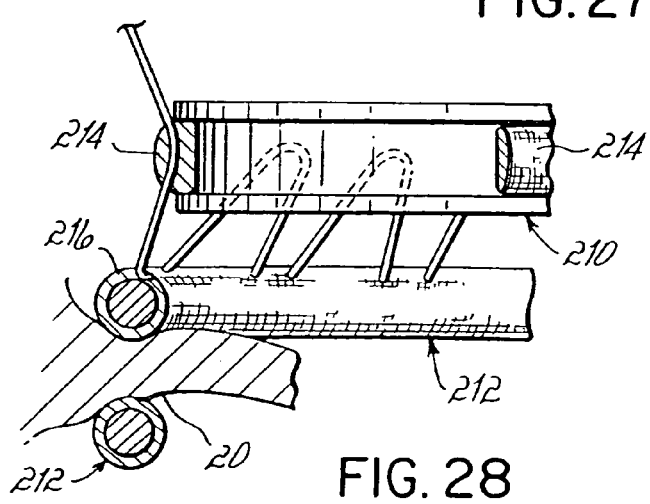
FIG. 28 is a fragmented, cross sectional view of another alternative heart valve repair device.

FIG. 28 illustrates another manner of securing a replacement heart valve 210 to a coil-type support member 212 constructed in accordance with the invention as previously described. In this embodiment, the replacement valve 210 includes a cuff 214, for example, formed from a fabric and the coil-type support member 212 also includes a fabric cuff 216. The surgeon stitches the replacement valve 210 into place by suturing between the two cuffs 214, 216 with, for example, known suturing methods allowing the suture to be pulled tight to engage the two cuffs 214, 216 together and thereby form a seal.

FIGS. 29 and 29A illustrate an alternative coil-type support member 217 formed from a flat piece of material, such as metal or plastic. FIG. 29B also illustrates an alternative coil-type support member 218 formed generally from a flat piece of material, such as metal or plastic, and having one substantially planar coil 218a and an adjacent undulating coil 218b.

FIG. 30 illustrates another alternative coil-type support member 219 affixed to an annulus 20 of a mitral valve 18 and including yet another distinct cross-sectional configuration. In particular, an upper coil includes a recess 219a and a lower coil includes a projection 219b received in recess 219a and trapping tissue 20 therein. This may be desirable for gathering up excess annulus tissue.

FIGS. 31 and 32 illustrates another modification to a coil-type support member 220 adapted to be secured around the annulus 20 of a valve, such as a mitral valve 18. In this embodiment, each end of the coil-type support member 220 is turned or bent in an opposite direction. One end 220a is a starting end and is tapered for easier insertion into a small slit or hole 222 formed by the surgeon in the valve annulus 20. Another end 220b is turned upwardly for engagement by a suitable tool 224 used by the surgeon to turn the support member 220 into place around the valve annulus 20 as generally described above.

FIG. 33 illustrates a cross section of one coil 226 of a coil-type support member showing an alternative cross-sectional construction. In this regard, the coil 226 may be formed from a core 228 comprising low friction material, such as a low friction polymer, to expose a lower surface 228a for engagement with the annulus tissue (not shown) while the coil 226 is turned into place as generally described above. An outer surface or exposed surface 228b may be covered with a suitable fabric 230 such as a conventional fabric used on annuloplasty rings. This fabric may be connected to the core 228 using suitable pins or staples 232 or by other fixation methods.

Figure 34A:
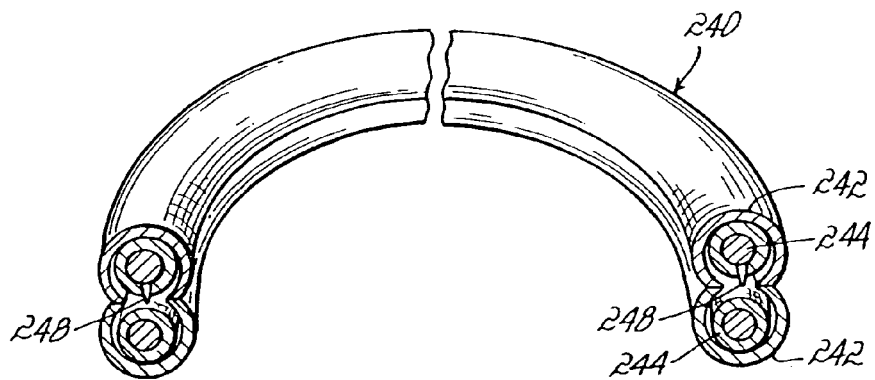
FIG. 34A is a sectioned, perspective view of another alternative heart valve repair device.
Figure 34B:
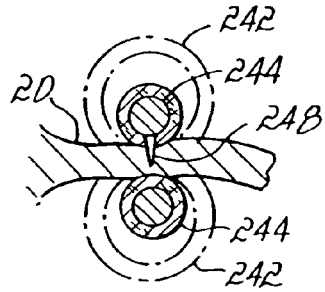
FIG. 34B is a cross sectional view of the device shown in FIG. 34A and illustrating connection thereof to valve tissue.

FIGS. 34A and 34B illustrate another alternative embodiment showing a coil-type support member 240 in cross section comprised of an outer hollow carrier 242, which may be formed from a metal or generally rigid plastic, for example, and which holds a core portion 244. The coil support member 240 may be turned into place above and below a valve annulus 20, as previously described. With the outer carrier 242 in place as shown in FIG. 34A, the internal core portion 244, which also has the configuration of a coil, is held apart against its own natural bias to remain together with closely adjacent coils. When the hollow carrier 242 is removed as shown in FIG. 34B, the internal core portion 244 springs together to its initial position and a plurality of projections, spikes or barbs 248 are driven into the valve annulus tissue 20 as shown in FIG. 34B. These spikes 248 may penetrate completely through the tissue 20 or only partially as shown.

Figure 35A:
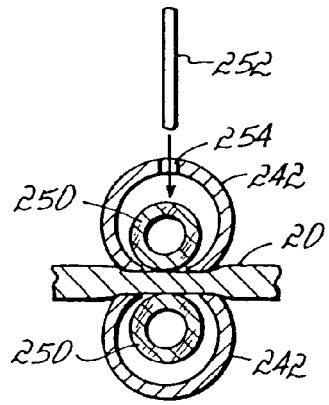
FIG. 35A is a cross sectional view similar to FIG. 34B, but illustrating an alternative fastening system.
Figure 35B:
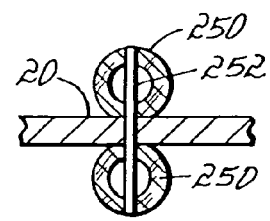
FIG. 35B is a cross sectional view similar to FIG. 35A, but illustrating the repair device fastened to the valve tissue.

Another alternative is shown in FIGS. 35A and 35B. In this regard, the outer carrier 242 carries an internal fabric core 250 and, after the carrier 242 and core 250 are turned into place around the valve annulus 20 as shown in the cross section of FIG. 35A, a plurality of pins 252 are driven through holes 254 in the carrier 242 and also through the fabric core 250 disposed on opposite sides of the valve annulus 20, as well as the valve annulus itself as shown in FIG. 35B. After pins 252 are inserted around the entire circumference of the valve annulus 20, the carrier 242 is turned out of position and removed to leave the fixed core 250 in place above and below the valve annulus 20 as shown in FIG. 35B.

Figure 36:
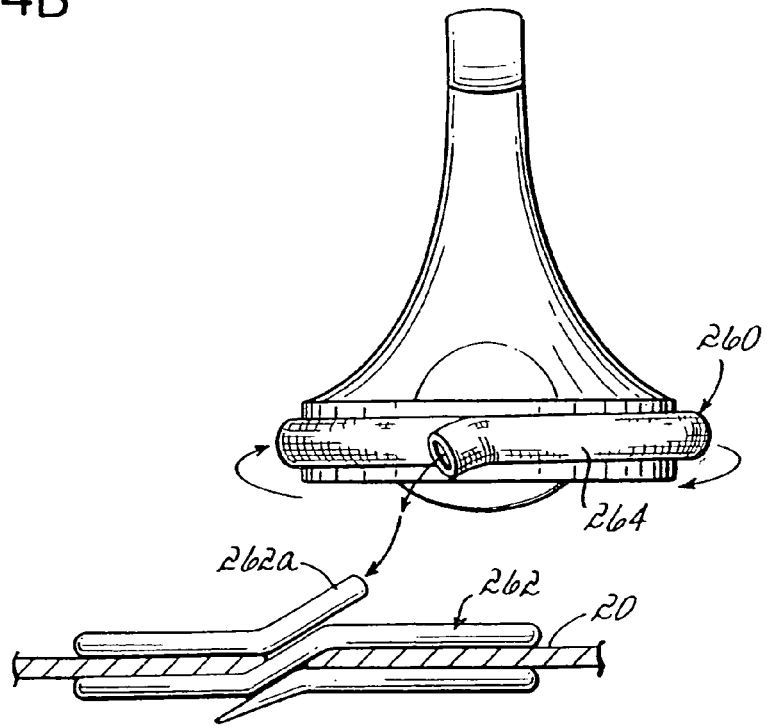
FIG. 36 is a side elevational view showing another alternative heart valve replacement device of the invention.
Figure 37:
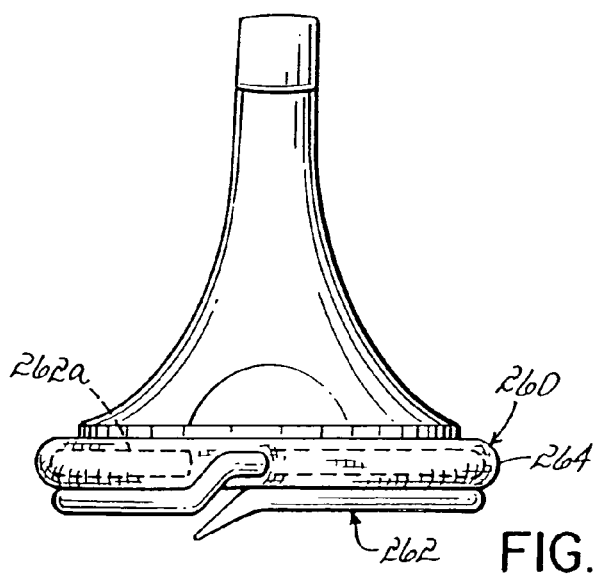
FIG. 37 is a side elevational view similar to FIG. 36, but illustrating full connection between the replacement valve and coil support member.

FIG. 36 illustrates the insertion of a replacement valve 260 onto a coil-type support member 262 fixed to a valve annulus 20. In this embodiment, the replacement valve 260 includes a cuff 264 on its outer periphery which receives an upper coil 262a of the support member 262 when turned in place as shown in FIG. 37. It will be appreciated that the male-female coupling of cuff 264 and coil 262a could be reversed, e.g., coil 262a could carry a cuff which receives a coil or ring on valve 260.

Figure 38:
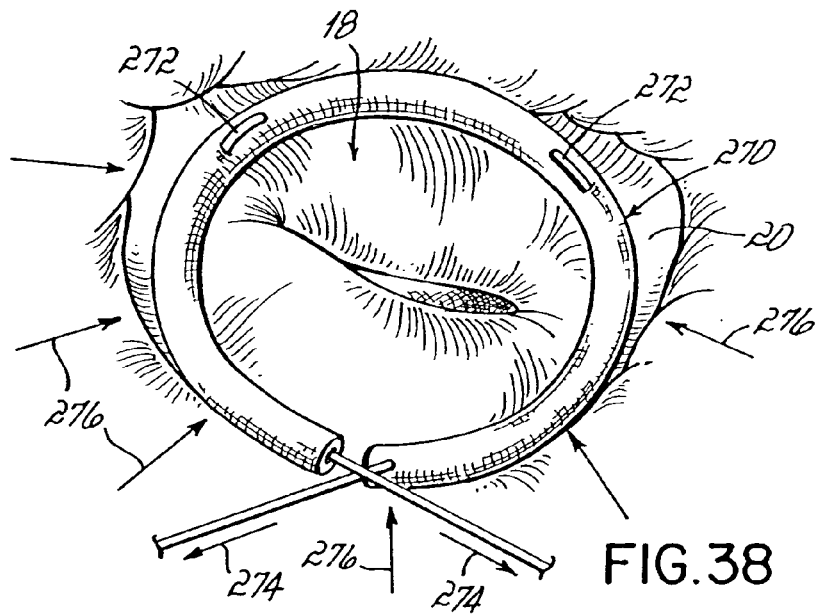
FIG. 38 is a top view of a mitral valve and an alternative heart valve repair device applied thereto.

FIG. 38 illustrates another coil-type support member 270 secured around a mitral valve 18 and including an internal drawstring 272 which may be pulled in the direction of arrows 274 to reduce the diameter of the support member 270 and correspondingly reduce the diameter of the mitral valve 18 as shown by arrows 276. The drawstring 272 may be tied to secure the valve 18 at the desired diameter.

Figure 39A:
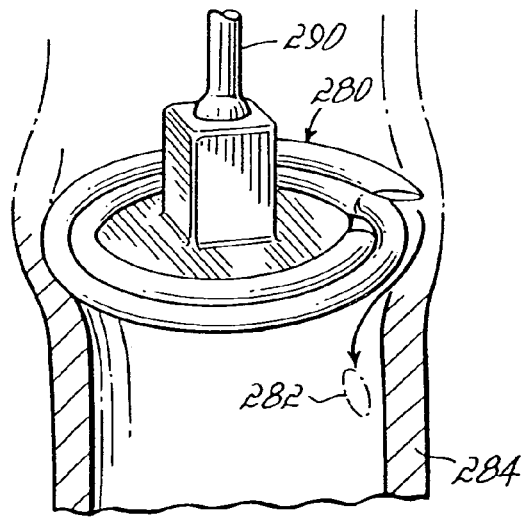
FIGS. 39A–D are schematic views illustrating the process steps for replacing a valve in accordance with another embodiment of the invention.
Figure 39B:
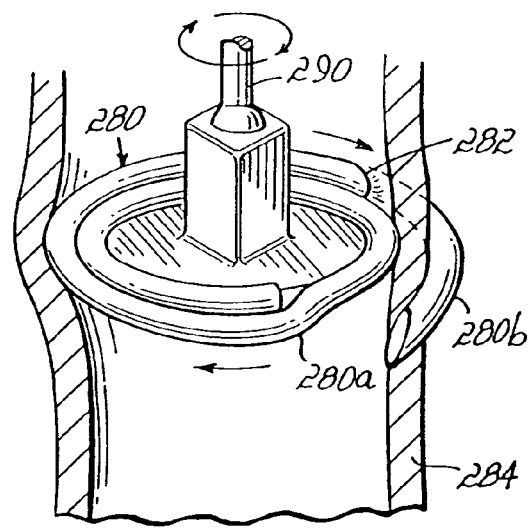
Figure 39C:
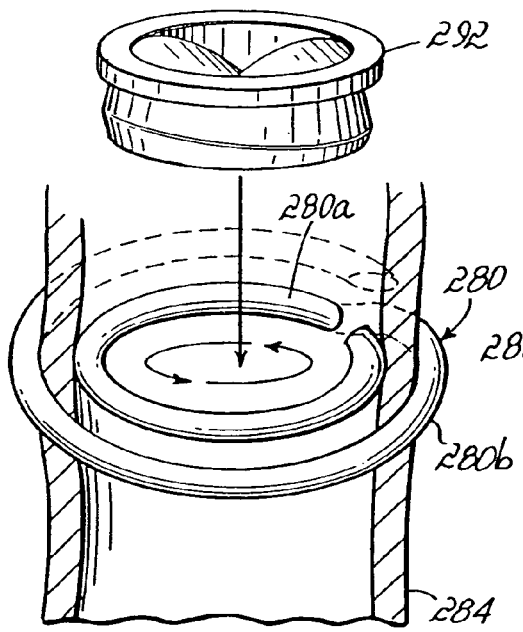
Figure 39D:
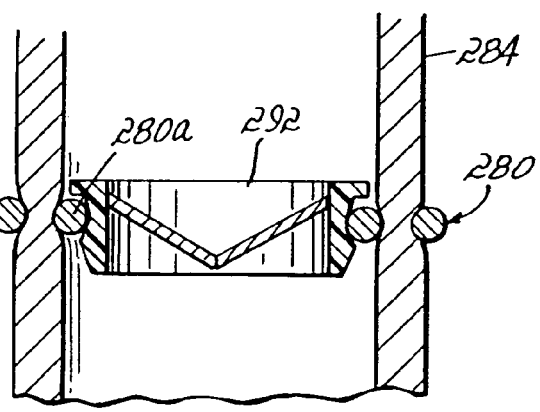

FIGS. 39A–39D illustrate another alternative coil-type support member 280. In this embodiment the coils 280a, 280b are at least substantially concentric such that the support member 280 may be turned through a hole 282 in a vessel 284 and the coils 280a, 280b engage and trap the vessel 284 between the adjacent coils 280a, 280b. In the embodiment shown, a carrier 290 is used to turn the support member 280 into place as shown in FIGS. 39A and 39B and a replacement valve 292 may then be secured within the inner coil 280a as schematically shown in FIGS. 39C and 39D using one of the fixation methods described above or another suitable fixation method.

Figure 40:
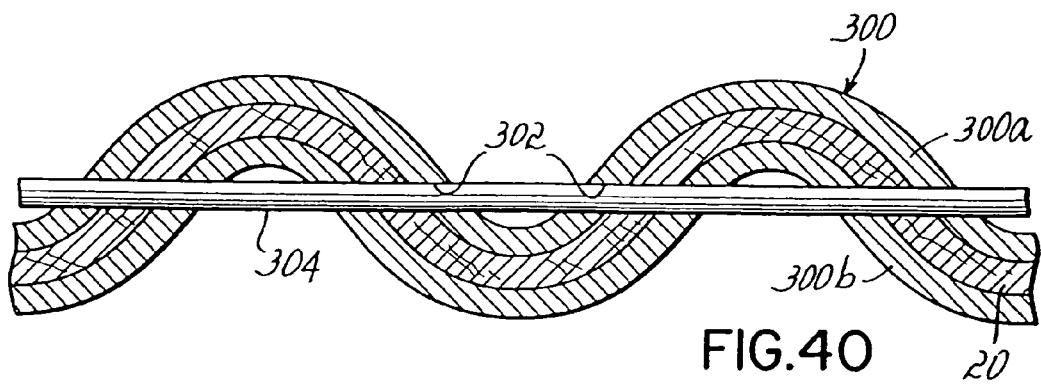
FIG. 40 is a cross sectional view illustrating another alternative heart valve repair device.

FIG. 40 illustrates an undulating coil-type support member 300 shown in cross section having adjacent coils 300a, 300b trapping tissue, such as annulus tissue 20, therebetween. The construction of the support member 300 would otherwise be similar to the constructions described above. The undulations provide a manner of further securing the support member 300 to the tissue 20. As an additional securement method, the coils may contain aligned holes 302 for receiving, for example, a suture 304 through portions of the coil 300 and tissue 20 or through the entire circumferential extent of coil 300 for additional securement.

FIGS. 41A and 41B illustrate another alternative embodiment in which a coil member 310, for example, formed from a metal or relatively rigid plastic is used as a carrier for a fabric support member 312. The fabric support member 312 may also be coil-shaped and, therefore, ultimately reside on both sides of annulus 20 or, alternatively, be ring-shaped or otherwise shaped to only reside on one side of annulus 20 similar to conventional annuloplasty rings. In this regard, the fabric support member 312 may be temporarily sutured to the coil carrier 310 and the combination is turned into place above and below the valve annulus tissue 20. A lower coil 310a includes an anvil or recess 314, for example, and, once the combination 310, 312 is turned into place as shown in FIG. 41A, a series of staples 316 may be deposited through the fabric support member 312 to secure the fabric support member 312 to the valve annulus 20 as shown in FIG. 41B. When a requisite number of staples 316 has been applied around the valve annulus 20, the coil carrier 310 may be turned out and removed after removing the temporary sutures (not shown) leaving the fabric support member 312 in place around all or a portion of valve annulus 20.

As illustrated in FIG. 42, another alternative heart valve replacement device 330 comprises a replacement valve having a pair of flaps 332, 334 coupled with an annular support member 336. It will be appreciated that each of the replacement valves is illustrated herein schematically and these valves may take many different forms as is generally know in the art. A coil-shaped member 340 constructed generally as described for the previous embodiments of coil-shaped repair devices is secured around valve annulus 20. In this embodiment, device 340 may comprise a coil having an inner core 342 and an outer layer or cuff 344. Cuff 344 contains a fastening ring 346 which is secured beneath a lip 336a of annular support member 336. In FIG. 42, fastening ring 346 is shown engaged on the right-hand side and in the process of moving radially inward into engagement on the left-hand side. This engagement, for example, may occur through the use of a shape memory alloy which may be activated, for example, through the suitable application of electric current into fastening member 346 to move fastening member 346 into the fully engaged position beneath lip 336a.

FIG. 43 illustrates another alternative heart valve replacement system including a replacement valve 350 including an annular fabric cuff 352. Cuff 352 receives sutures 354 which extend further through a cuff 360 associated with a coil-shaped device 362, such as one of the devices described above. At one point, cuff 352 is secured to cuff 360 by a hinge structure 364, which may also be formed with sutures. By suturing cuff 352 to cuff 360 around the entire annulus and pulling suture 354 taught, a sealing engagement is formed between cuff 352 and cuff 360 thereby fastening replacement valve 350 to device 362. The existing leaflets of mitral valve 18 are removed by the surgeon prior to fastening replacement valve 350 to device 362.

What is claimed is:

1. A device for repairing a heart valve comprised of valve tissue including an annulus and a plurality of leaflets for allowing and preventing blood flow, the device comprising:
   a catheter having a lumen and an open end,
   an elongate valve support member carried within said lumen and movable from said open end, said elongate valve support member having an uncoiled configuration within said lumen and assuming a coiled configuration when extended from said open end, wherein a first portion of said elongate valve support member in the coiled configuration is configured to abut one side of the valve and a second portion of said elongate valve support member in the coiled configuration is configured to abut an opposite side of the valve, whereby a portion of the valve tissue is trapped between said first and second portions.

2. The device of claim 1, wherein said elongate valve support member includes an inner core covered by an outer layer, said inner core formed from a more rigid material than said outer layer.

3. The device of claim 1, wherein said elongate valve support member has a generally triangular-shaped cross section.

4. The device of claim 1 further comprising:
   an actuator carried within said lumen and operable to extend said elongate valve support member from said open end.

5. The device of claim 4, wherein said actuator further comprises a gripping element operable to grip and allow releasing of one end of said elongate valve support member.

6. The device of claim 1, wherein said elongate valve support member is formed from a shape memory alloy.

* * * * *

UNITED STATES PATENT AND TRADEMARK OFFICE
CERTIFICATE OF CORRECTION

PATENT NO. : 6,964,684 B2  
APPLICATION NO. : 10/787581  
DATED : November 15, 2005  
INVENTOR(S) : Mark Ortiz et al.

Page 1 of 1

It is certified that error appears in the above-identified patent and that said Letters Patent is hereby corrected as shown below:

Column 11, at line 12 insert the following paragraph:

--While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in numerous combinations depending on the needs and preferences of the user. This has been a description of the present invention, along with the preferred methods of practicing the present invention as currently known. However, the invention itself should only be defined by the appended claims, wherein we claim:--.

Signed and Sealed this

Fifth Day of February, 2008

JON W. DUDAS  
*Director of the United States Patent and Trademark Office*